(12) United States Patent
Wiktor

(10) Patent No.: US 8,973,424 B2
(45) Date of Patent: Mar. 10, 2015

(54) METHOD FOR DETECTING LEAKS, SYSTEM AND MEDICAL TREATING DEVICE

(75) Inventor: Christoph Wiktor, Gelnhausen (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 45 days.

(21) Appl. No.: 13/818,396

(22) PCT Filed: Aug. 24, 2011

(86) PCT No.: PCT/EP2011/004241
§ 371 (c)(1),
(2), (4) Date: Mar. 27, 2013

(87) PCT Pub. No.: WO2012/025225
PCT Pub. Date: Mar. 1, 2012

(65) Prior Publication Data
US 2013/0174650 A1    Jul. 11, 2013

(30) Foreign Application Priority Data
Aug. 25, 2010    (DE) .......................... 10 2010 035 498

(51) Int. Cl.
*G01M 3/28*    (2006.01)
*G01M 3/38*    (2006.01)
*A61M 1/16*    (2006.01)

(52) U.S. Cl.
CPC . *G01M 3/28* (2013.01); *A61M 1/16* (2013.01); *G01M 3/2846* (2013.01); *G01M 3/38* (2013.01); *A61M 2205/15* (2013.01); *A61M 2205/3306* (2013.01); *A61M 2205/705* (2013.01)
USPC .......................... 73/40.5 R; 73/40; 73/40.5 A

(58) Field of Classification Search
CPC . E21B 47/1025; E21B 47/101; E21B 47/102; G01M 3/007; A61M 2205/705; A61M 5/16831
USPC ........................................ 73/40, 40.5 R, 49.8
See application file for complete search history.

(56) References Cited

U.S. PATENT DOCUMENTS

| | | | | |
|---|---|---|---|---|
| 6,044,691 A | * | 4/2000 | Kenley et al. | 73/40.5 R |
| 6,740,036 B1 | * | 5/2004 | Lee et al. | 600/437 |
| 2003/0126910 A1 | * | 7/2003 | Burbank | 73/40 |

FOREIGN PATENT DOCUMENTS

| | | |
|---|---|---|
| DE | 3827913 A1 | 2/1990 |
| DE | 4333951 A1 | 4/1995 |

(Continued)

OTHER PUBLICATIONS

English translation for EP0646781.*

(Continued)

*Primary Examiner* — Peter Macchiarolo
*Assistant Examiner* — Anthony W Megna Fuentes
(74) *Attorney, Agent, or Firm* — Kenyon & Kenyon LLP

(57) ABSTRACT

The present invention relates to a method for detecting leakages in a system for conducting a medical fluid upstream a shut-off device of the system as well as systems related thereto. More specifically, the method is used with systems having a section conducting the medical fluid, the section being arranged upstream the shut-off device, which is configured to interrupt or reduce an escaping or outflow of the fluid out of the section into an area downstream the shut-off device. The system for use with the present method further has at least one conveying device for conveying the fluid through the section. The present invention further relates to a digital storage medium, a computer program product and a computer program for performing the method for detecting leakages.

23 Claims, 3 Drawing Sheets

(56) References Cited

FOREIGN PATENT DOCUMENTS

| | | | |
|---|---|---|---|
| DE | EP0646781 | * 4/1995 | ............. G01M 3/32 |
| DE | 10313166 A1 | 4/2004 | |
| DE | 102009026620 A1 | 12/2009 | |
| DE | 202010004669 U1 | 8/2010 | |
| EP | 0 631 757 B1 | 1/1995 | |
| EP | 0646781 A2 | 4/1995 | |
| EP | 1 666 864 A1 | 6/2006 | |

OTHER PUBLICATIONS

International Search Report from PCT/EP2011/004241 mailed on Dec. 23, 2011.

* cited by examiner

METHOD FOR DETECTING LEAKS, SYSTEM AND MEDICAL TREATING DEVICE

CROSS REFERENCE TO RELATED APPLICATIONS

This is a 371 national phase application of PCT/EP2011/004241 filed Aug. 24, 2011, which claims priority from German Patent Application No. 10 2010 035 498.8, filed Aug. 25, 2010.

FIELD OF INVENTION

The present invention relates to methods for detecting leakages in systems conducting a medical fluid, systems for detecting leakages, including medical-technical treatment apparatuses. The present invention also relates to digital storage media, computer program products, and computer programs for detecting such leakages.

BACKGROUND OF INVENTION

The occurrence of leakages in systems which conduct medical fluids may regularly be problematic or even dangerous. Early detection of such leakages is thus of great importance.

One object of the present invention is to propose a method suited for the detection of leakages. Furthermore, an appropriate system as well as a medical-technical treatment apparatus are to be provided.

All advantages achievable by means of the method according to the present invention may undiminishedly also be achieved by means of the system and/or the medical-technical treatment apparatus.

The method according to the present invention is suited and provided for the detection of leakages in a system conducting a medical fluid, in particular upstream a shut-off device of the system, the system comprising at least the following components: at least one conveying device, a shut-off device and a section conducting the medical fluid, the section being arranged upstream the shut-off device. The conveying device serves for conveying the fluid through the section of the system. This is feasible at least in the direction towards the shut-off device. Furthermore, the conveying device may optionally be designed or embodied, respectively, or arranged or configured in addition for conveying in the opposite direction.

The method according to the present invention encompasses interrupting or reducing a fluid flow of the medical fluid through or out of the section during a first conveying effort of the conveying device. In order to interrupt or reduce, the shut-off device is adjusted or set, respectively, accordingly, e.g., closed. In this adjustment setting, a first conveying state is reached.

Further, the method according to the present invention encompasses reaching a second conveying state in the section by changing the conveying effort of the conveying device; the first conveying effort turns into a second conveying effort.

In a further step, the method according to the present invention encompasses emitting at least one signal by means of a signal emitting device—both in the first and the second conveying state—into the section of the system (measurable, e.g., within the section by means of a sensor present therein) and, where appropriate, through the section (measurable, e.g., as a transmittance on the side of the section opposite to the signal incidence side, or as a reflexion on the side of the section from which the signal was emitted).

The proportion of the emitted signal leaving the section again in the first conveying state (or penetrating into the section and being received within the section by the signal reception device) is thereby received by means of a signal reception device, the said proportion in the following being referred to as first proportion. Analogously, the proportion of the emitted signal leaving the section again in the second conveying state (or penetrating into the section and being received within the section by the signal reception device) is thereby received by means of the signal reception device, the said proportion in the following being referred to as second proportion.

Subsequently, in a further step of the method according to the present invention, based on an evaluation of the first proportion in relation to the second proportion, a conclusion may be drawn whether or not a leakage is present or has occurred, respectively.

The system according to the present invention comprises at least one controller suited and/or configured and/or provided for executing the method according to the present invention.

The medical-technical or medical treatment apparatus according to the present invention is provided for being connected, or is connected, with at least one system according to the present invention. In addition or instead, the treatment apparatus according to the present invention is, in certain embodiments, provided or intended for executing at least one method according to the present invention.

Embodiments according to the present invention may comprise some or all of the following features in any arbitrary combination.

In some embodiments according to the present invention, the emitted signal encompasses or consists of ultrasonic waves. In such a case, the signal emitting device emits ultrasonic waves and the signal receiving device detects the ultrasonic waves. The system according to the present invention may be designed or embodied correspondingly.

In certain embodiments according to the present invention, the signal emitting device and/or the signal receiving device are or comprise piezoelectric crystals.

In some embodiments according to the present invention, the emitted signal encompasses or consists of radiation. In such a case, the signal emitting device is a radiation source for emitting radiation and the signal receiving device is a radiation receptor for receiving or detecting radiation. The system according to the present invention may be designed or embodied accordingly.

In certain embodiments according to the present invention, the signal emitting device and the signal receiving device are one and the same device. Such a device thus serves both for emitting and receiving the respective signal. Such an embodiment or construction according to the present invention may be realized regardless of the type of signal to be transmitted and received. A common or combined embodiment or construction of a signal emitting device and signal receiving device in one single device being able to vary after switching or reversing the operating principle between emitting and receiving is—like an embodiment or construction of signal emitting device and signal receiving device as separate devices but present in one common housing—both when using ultrasound and when using other types of signals subject-matter of embodiments according to the present invention.

The present invention may, without, however, being limited hereto, advantageously be used for detecting leakages in an extracorporeal blood circuit and/or leaking connectors in or at a blood treatment apparatus such as, e.g., a dialyzer.

The term "system" as used herein in certain embodiments of the present invention refers to a (medical-)technical system—as opposed to a vascular system of a patient.

In certain embodiments of the present invention, the system comprises an arrangement of several components such as lines, tubes, channels, flow-promoting and/or flow-reducing elements, supply devices and/or drain devices, and the like, the arrangement being suited and/or provided or intended for conducting fluids. In certain embodiments, the system is designed or embodied, for instance, as a tube system such as an extracorporeal blood circuit without, however, being limited hereto.

The system is designed or embodied and/or provided or intended for receiving and/or conducting at least one medical fluid by means of a section contained in the system, such as an interior, e.g., a line interior, of the system.

The term "medical fluid" as used herein in certain embodiments according to the present invention refers to a fluid which is present or flowing extracorporeally and—e.g., during an extracorporeal blood treatment—is preferably to be treated.

The medical fluid in some embodiments according to the present invention is a liquid such as blood, dialysate, substituate, drug solutions, a gas, or a combination or mixture thereof.

The term "section" as used herein in certain embodiments according to the present invention refers to a part or portion or segment or section, respectively, of the system in which the leakage to be detected occurs or is to be ruled out.

The term "leakage" as used herein refers to a leak, an—unwanted—opening, a leakiness or a hole within the fluid-conducting system, in particular of the section through which the fluid conducted within the system may unwantedly escape from the system's interior to an exterior of the system. The occurrence of leakages may have arbitrary causes; these causes as such are irrelevant as regards the present invention.

The term "shut-off device" as used herein refers to a device or means, respectively, arranged at or on, respectively, or in the system, the device or means, respectively, being suited and/or provided or intended for reducing or interrupting or preventing, respectively, a streaming or a flow of the medical fluid through at least one section of the system.

In certain embodiments of the present invention, the shut-off device is intended or provided for interrupting or reducing an escaping or flowing of the fluid from or out of the section into an area downstream the shut-off device.

The term "downstream" in certain embodiments according to the present invention is to be understood as a streaming direction within the section, which when executing the method as described herein leads away from the conveying device.

The shut-off device may, without being limited hereto, be a clamp, such as an arterial clamp or a venous clamp of an extracorporeal blood circuit, an inductor or choke, respectively, a valve, a shut-off valve, and the like, or may comprise one or more such elements. It may be one piece or comprise several parts. The shut-off or barrier effect of the shut-off device may be a result of the interaction of several, i.e., multiple, shut-off components, or, however, solely of one single shut-off component.

The term "conveying device" as used herein in certain embodiments according to the present invention refers to a device or means, respectively, suited and/or provided or intended for conveying the medical fluid within an interior of the system or a section thereof, respectively, or through or along the interior or the section. Conveying the medical fluid may be effected indirectly or directly.

The concrete design or arrangement or construction, respectively, of the conveying device is not limited according to the present invention. Non-limiting examples include non-occluding pumps such as a centrifugal pump, and the like.

The term "conveying effort" as used herein in certain embodiments of the present invention, in certain embodiments according to the present invention relates to an output or effort or performance, respectively, or work performed by the conveying device for conveying the medical fluid. This may be measured by means of, e.g., a voltage metering or a current measurement at the inlet of the conveying device.

In some embodiments according to the present invention, the conveying effort corresponds to a conveying output or performance, respectively, (e.g., in milliliters per minute, ml/min) which would be conveyed within the section by means of the conveying device in case the shut-off device being open.

In some embodiments according to the present invention, the conveying effort corresponds to a characteristic of the conveying device variable during the use of the conveying device. This includes a set or targeted or intended or conducted number of revolutions per minute of the conveying device.

A conveying effort in certain embodiments of the present invention refers to a state of the conveying device during conveying the medical fluid, in particular a state for which the conveying device was adjusted for conveying the medical fluid, e.g., by setting or specifying, respectively, certain parameters such as a conveying pressure, a conveying output or performance, a conveying speed, and the like.

"Changing a conveying effort", e.g., changing the first conveying effort to become a second conveying effort, may be achieved by changing at least one of the parameters set or adjusted, respectively, or settable or adjustable, respectively, for a conveying state, such as, for example, by changing the rotational speed.

Thereby, the—first and/or second—conveying effort performed by the conveying device may be constant or not constant. Preferably, the first and/or second conveying effort performed by the conveying device is substantially or completely constant.

The terms first and second "conveying state" in certain embodiments according to the present invention describe the state appearing in relation to a first and second flow rate downstream the shut-off device appearing in the section as a result of both the conveying effort of the conveying device and the barrier effect of the shut-off device.

The first conveying state and the second conveying state may be the same or different. At least one of the two conveying states may be zero.

Thus, a first conveying state may be zero, expressed, e.g., by a flow of 0 ml/min, measured or at least measurable downstream the shut-off device. This may be a result of a complete shut-off of a flow across the shut-off device. Likewise, a second conveying state may be zero which may, e.g., be a result of a complete stop of the conveying device. However, the present invention is not limited to measurements or examinations or analyses, respectively, during complete shut-off by means of the shut-off device or complete interruption of the fluid flow by stopping the conveying device, or feasible only in this way, as is recognizable for the skilled person. Rather, it is also possible to achieve the advantages of the method according to the present invention with the shut-off device being only partly shut or closed, respectively, and accordingly only partial throttling of the conveying device. These embodiments are encompassed by the present invention as well. This is expressed by the use of the term "conveying state" as described above.

In certain embodiments, the present invention encompasses that initially a first conveying state is considered, and subsequently the second conveying state. However, the present invention is not limited hereto. For instance, the order of the examination or measurement is arbitrary as can also be taken from FIGS. 2 to 5. For example, in some embodiments initially the conveying device may be stopped or throttled and only after that the shut-off device may be shut off or throttled, or vice versa.

In certain embodiments of the present invention, the emitted radiation—wherein radiation here is to be understood as an example for a signal as used herein—is or encompasses electromagnetic radiation such as visible light.

In certain embodiments of the present invention, the emitted radiation is or encompasses infrared radiation, e.g., from a narrowband infrared light source. A peak wavelength of the infrared radiation is preferably approximately or exactly 805 nm.

The term "radiation receptor" as used herein in certain embodiments of the present invention refers to a device or a means or a sensor, respectively, which is suited and/or provided or intended and/or designed or embodied for receiving and/or detecting the radiation emitted out of the section of the system.

Non-limiting examples of radiation receptors include optical detectors such as a photodiode, a photoconductive cell or a photo transistor, and the like.

The radiation receptor may, like the radiation source, be designed or embodied in one piece or consisting of or comprising several parts and/or may be designed or embodied by means of one or more component(s) for receiving and/or emitting radiation. In some embodiments of the present invention, the radiation receptor is provided or intended and designed or embodied as an individual and/or independent component. In some embodiments of the present invention, the radiation receptor is provided in one shared or common physical arrangement such as a shared or common housing together with the radiation source.

The term "signal receiving device" as used herein goes beyond the term "radiation receptor" as described above as regards content. A signal receiving device may be a radiation receptor; however, it is not limited to receiving radiation. Instead of—or in addition to—radiation, another signal, e.g., an ultrasonic signal, may be received. The same relation applies to the terms "radiation source" and "signal emitting device".

The term "receiving" a proportion of the emitted signal, e.g., of the emitted radiation as used herein in certain embodiments of the present invention refers to a targeted reception or detection of the signal emitted out of the section of the system, e.g., the emitted radiation.

The "proportion of the emitted signal" may be a proportion of a signal, e.g., radiation, which leaves the section—e.g., by reflexion, transmittance, scattering etc.—or a proportion of a signal, e.g., radiation, which has penetrated the section and was measured therein.

The term "proportion" as used herein in certain embodiments of the present invention refers to a part or portion, respectively, e.g., a fractional part or subset, to which the received signal, e.g., the received radiation, amounts in relation to the originally emitted signal.

The proportion of the emitted signal, e.g., radiation, which is received again after emission, in some embodiments according to the present invention is a fractional part of an intensity (measured, e.g., as amplitude of a signal, as counts, as counts per time unit, as electric potential after corresponding conversion, electric current, frequency, etc.).

Counts may thereby, without being limited hereto, be obtained as follows: When using a signal receiving device which is designed or embodied as a photo receiver which operates as a light-to-frequency-converter, the sensor used delivers a frequency proportional to the received light intensity. For the evaluation, e.g., the edges of the signal are counted over a certain time unit; each edge is thereby classified as a count.

In some embodiments of the present invention, this proportion of the emitted signal or of the emitted radiation leaving the system or the section of the system, respectively, is exclusively or also a reflected signal. In some embodiments of the present invention, the proportion of the emitted signal or of the emitted radiation leaving the system or the section of the system, respectively, is exclusively or also a transmitted signal. In certain embodiments of the present invention, the proportion of the emitted signal, e.g., of the emitted radiation, leaving the system or the section of the system, respectively, is an exclusively or also scattered, e.g., sidewards or laterally scattered, signal, e.g., radiation.

For drawing a conclusion whether a leakage is present, by means of an evaluation of the first proportion in relation to the second proportion, in certain embodiments according to the present invention a comparison of the first proportion and the second proportion, or of the amounts or levels or extents or the characteristics, respectively, is intended or provided.

The comparison of the first proportion and the second proportion in certain embodiments of the present invention is made by comparing a first average value of a first received signal received as a first proportion over a certain first time period to a second average value of a second received signal received as a second proportion over a certain second time period.

In some embodiments of the present invention, the comparison is made by subtracting the first proportion or the average value of the first proportion from the second proportion or the average value of the second proportion in order to obtain a difference or a difference value.

In some embodiments, the comparison is made by comparing signal spectra or radiation spectra of the first and the second proportion of the received signal or of the received radiation. For example, the absolute values of signal maxima or radiation maxima and/or signal minima or radiation minima of the recorded signal spectra or radiation spectra may be compared.

In some embodiments of the present invention, the comparison is made by establishing a relation between the first proportion or the first average value thereof and the second proportion or the second average value thereof.

In certain embodiments of the present invention, drawing a conclusion whether a leakage is present encompasses or consists of a comparison with a threshold value. Thereby, a difference, a relation or a value derived in any other way may be compared with the threshold value. The difference or the relation may in particular be determined as described above.

The threshold value may in particular be a predetermined threshold value or reference value such as, for example, a threshold value detected, calculated, estimated, or the like, in a system or a section, respectively, without leakage.

In certain embodiments of the present invention, the first and/or the second proportion is or reflects a percentage signal intensity or radiation intensity (I).

In certain embodiments of the present invention, the signal reception device, in particular when being designed or embodied as radiation receptor, is used for detecting an optical density or a change hereof. The latter may serve for detecting a leakage but is, however, not mandatorily necessary.

In such embodiments, it may, for example, advantageously be possible to differentiate between the presence of blood or water in an extracorporeal blood circuit.

In order to execute the method according to the present invention, in certain embodiments according to the present invention a fluid flow of the medical fluid through the section of the system in the first conveying state is stopped by means of the shut-off device. The flow may be stopped, i.e., be set to zero. In other embodiments according to the present invention, the fluid flow is only appropriately reduced or throttled by means of the shut-off device, however, not completely stopped.

In such a case, the conveying device may or may not continue conveying.

In certain embodiments of the method according to the present invention, it is intended to stop the conveying device in the second conveying state. In other embodiments according to the present invention, the conveying device is only throttled, however, not completely stopped.

In certain embodiments of the present invention, it is intended to issue an alarm if executing the method according to the present invention would lead to the result or the assumption that a leakage is present in the fluid-conducting system. Depending on the wish or request and/or the demand or requirement, respectively, the alarm may be an optical alarm, an acoustic alarm or any arbitrarily suited alarm as well as a combination of different alarms.

All, a few or some steps of a method according to the present invention as described exemplarily and in a non-limiting way with regard to the appended drawing may be performed automatically. For each of the procedural steps as described in relation to the method according to the present invention, the apparatuses according to the present invention may comprise corresponding devices for the implementation thereof.

In certain embodiments of the present invention, the system according to the present invention comprises at least one treatment cassette comprising at least one section conducting a medical fluid, a conveying device for conveying the fluid through the section as well as a shut-off device for interrupting or reducing the fluid flow through the section.

The term "treatment cassette" as used herein refers to a functional device that is intended or provided and/or is or will be used for performing a medical treatment, e.g., an extracorporeal blood treatment.

Examples of treatment cassettes include a blood cassette, e.g., in form of a cast part or an injection-molded part, irrespective of whether or not the blood cassette is designed or embodied as a one-way article or a disposable.

In certain embodiments of the system according to the present invention, at least the conveying device is part of the treatment cassette.

The system according to the present invention in certain embodiments comprises a radiation source for emitting radiation as a signal emitting device.

The radiation source in certain embodiments is designed or embodied for emitting electromagnetic radiation, in particular infrared light.

The signal emitting device in some embodiments is embodied or designed for emitting ultrasonic waves.

In certain embodiments according to the present invention, the system comprises a signal receiving device configured and/or provided or intended for receiving a proportion of the emitted signal and a controller for executing the method according to the present invention.

In certain embodiments, the signal receiving device is configured and/or provided or intended and/or designed or embodied for detecting reflected and/or transmitted and/or scattered signals.

In certain embodiments according to the present invention, the signal receiving device is designed or embodied as a device for receiving ultrasonic waves.

In some embodiments according to the present invention, the signal receiving device is designed or embodied as a device for receiving radiation.

The system according to the present invention in certain embodiments further comprises at least one comparing device for comparing the first proportion received in the first conveying state to the second proportion of the emitted signal, e.g., of the emitted radiation and/or of the ultrasonic waves, received in the second conveying state.

In certain embodiments of the system according to the present invention, further a decision device configured and/or provided or intended for drawing a conclusion whether a leakage is present in or within, respectively, or at or on, respectively, the system by means of an evaluation of the first proportion in relation to the second proportion.

In certain embodiments, the system further comprises at least one alarming device configured for issuing an alarm when a leakage is detected.

In some embodiments according to the present invention no gas-pump and/or no flow-meter for measuring the gas flow are used or provided, and/or no gas flow is measured.

In certain embodiments according to the present invention no negative pressure is applied during the execution of the method according to the present invention. Accordingly, in some embodiments according to the present invention no devices for applying negative pressure are provided and/or are used during the execution of method according to the present invention.

In some embodiments according to the present invention no result in absolute numbers is received or established.

In certain embodiments according to the present invention no flowrate is measured or determined.

The object according to the present invention is further also solved by a digital storage medium, a computer program product and a computer program.

A digital storage medium, in particular in the form of a disk, CD or DVD, having electrically readable control signals, may interact with a programmable computer system such that the execution of the technical steps of a method according to the present invention is prompted.

Thereby, all, a few or some of the technically executed steps of the method according to the present invention may be prompted.

A computer program product comprises a program code stored on a machine-readable medium for prompting the execution of the technical steps of the method according to the present invention when executing the computer program product on a computer.

The term "machine-readable medium" as used herein in certain embodiments of the present invention refers to a medium containing data or information which is interpretable by software and/or hardware. The medium may be a data medium such as a disk, a CD, DVD, a USB flash-drive, a flashcard, an SD card, and the like.

A computer program comprises a program code for prompting the execution of the technical steps of a method according to the present invention when executing the computer program on a computer.

It applies also to the computer program product and the computer program that all, a few or some of the technically performed steps of the method according to the present invention are prompted.

Certain embodiments according to the present invention comprise one or more of the following advantages.

The present invention provides a method and apparatuses by means of which in some embodiments according to the present invention the detection of leakages—irrespective of which cause—in fluid-conducting systems is advantageously and in a simple manner possible.

As the intensity of the detected signal, e.g., of the detected radiation, of the flowing blood differs from that of non-flowing or still-standing blood, it may, in certain embodiments of the present invention, for example, in an advantageously simple manner be possible to observe or optically detect, respectively, a change in the distribution of blood cells within the section of the system, and, due to the change, easily deduce a leakage in the blood-conducting system.

Pressure-holding or maintenance tests which are usually established for checking the leak tightness of fluid-conducting systems comprising occluding pumps such as roller pumps, hose pumps, displacement pumps etc., are, due to the underlying principle, not feasible for detecting leakages with constant pressure sources, i.e., non-occluding pumps such as centrifugal pumps, as the pressure will be constant also with small leakages being present. For such systems with non-occluding pumps, the present invention advantageously offers a simple and little elaborate possibility of detecting leakages nevertheless.

The use of an optical sensor may hereby in particular be of advantage for achieving greater accuracy also in case of small leakages, which is not possible by, e.g., flow sensors.

Additionally, the optical sensor used according to the present invention is an advantageously simple sensor which may at the same time contribute to reducing the constructional and/or financial effort associated with the system.

Furthermore, in certain embodiments of the present invention it may advantageously be possible to conduct further measurements such as, for example, a differentiation between blood and water and/or air or measurements of hematocrit hemoglobin concentrations, respectively, and the like while using one and the same sensor which may also be used for executing the method according to the present invention.

BRIEF DESCRIPTION OF THE DRAWINGS

In the following, the present invention is described merely exemplarily with regard to the appended figures. In the drawing, same reference numerals refer to same or identical elements. It applies.

DETAILED DESCRIPTION

For clarification of the method according to the present invention, the time intervals of the measurements in the following exemplary embodiments were chosen to be very long in order to obtain a presentation as illustrative and clear as possible for the purpose of describing the present invention. The duration for executing the method according to the present invention may, of course, be (considerably) shorter.

The following examples are furthermore explained by means of radiation as a signal. It is recognizable for the skilled person that the present invention is not limited to the use of radiation as a signal. Instead of radiation, rather also another type of signal may be used, as described above.

Figure 1:
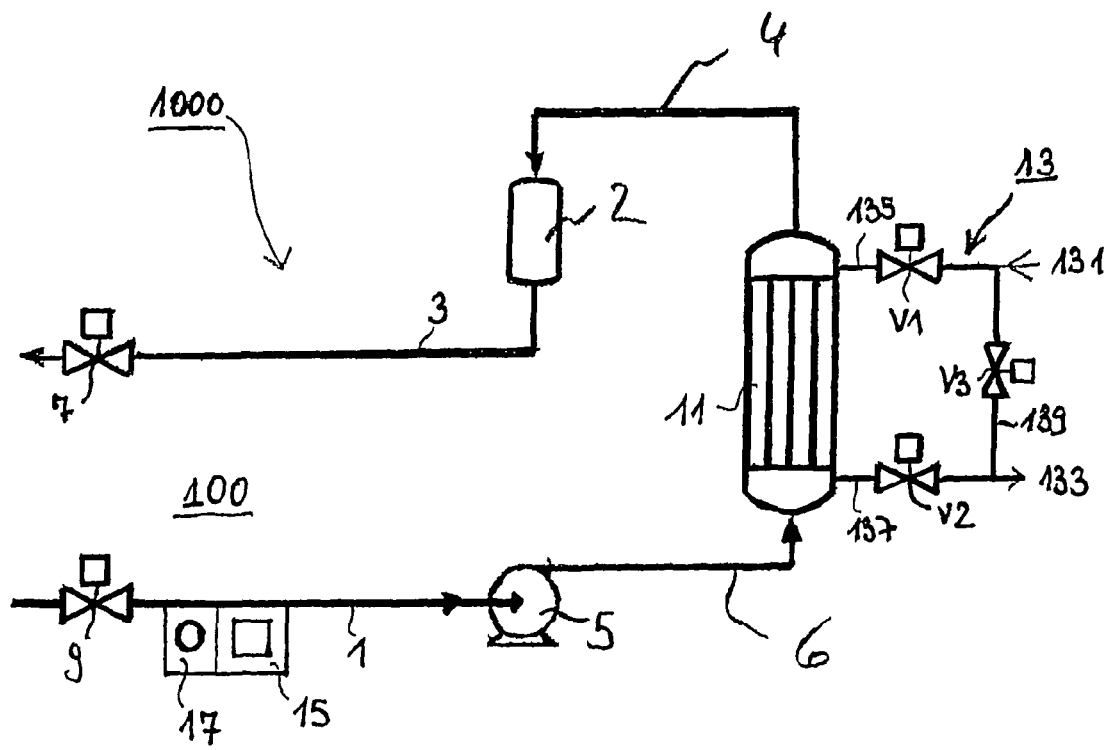
FIG. 1 schematically shows a section of a system according to the present invention.

FIG. 1 schematically shows a section of a system 1000 according to the present invention.

As shown in FIG. 1, the system 1000 is embodied as an extracorporeal blood circuit. The system 1000 may comprise or be a (e.g., plastic) tubing set.

The system comprises an arterial blood line 1 and a venous blood line 3 comprising a venous chamber 31.

For conveying blood in an interior of a line of the extracorporeal blood circuit, a conveying device 5, e.g., in form of a centrifugal pump or any other design or construction, which, e.g., is overflowable or non-occluding, is provided.

The venous leg of the extracorporeal blood circuit comprises a drip chamber 2. The drip chamber 2 comprises a conventional ventilation device, which is not shown. The ventilation device in some embodiments according to the present invention is an air extraction valve. In certain embodiments according to the present invention, the ventilation device comprises a membrane, preferably a hydrophobic membrane.

In FIG. 1, the direction of the extracorporeal flow of the blood within the line interior of the extracorporeal blood circuit during a blood treatment is indicated by means of the filled arrowheads.

The system 1000 comprises a venous clamp which in the frame of the embodiment according to the present invention of FIG. 1 exemplarily serves as a shut-off device 7.

The system 1000 further comprises an arterial clamp 9. The arterial clamp 9 may, but does not have to, be used additionally or alternatively to the shut-off device 7, as a shut-off device in the frame of the present invention.

For the extracorporeal blood treatment, a blood treatment device 11 is arranged in or within or is in fluid contact with, respectively, the extracorporeal blood circuit.

In the example of FIG. 1, the blood treatment device 11 is connected with the drip chamber 2 by means of a venous line section 4. Further, it is connected with the conveying device 5 by means of an arterial line section 6.

Examples for the blood treatment device 11 encompass a blood filter for cleaning a patient's blood during a hemodialysis treatment and/or a hemofiltration treatment, and the like, but are not limited hereto. The blood treatment device 11 may be designed as a one-way product or a disposable device.

The blood treatment device 11 further is in fluid contact with a dialysate circuit 13.

The dialysate circuit 13 comprises a dialysate inlet 131 and a dialysate outlet 133 or is connected with devices suited and/or provided for supplying or discharging, respectively, dialysate, respectively. The dialysate circuit 13 comprises a conventional dialysate pump not shown in FIG. 1 for conveying dialysate within the dialysate circuit 13.

In the supply line 135 leading from the dialysate inlet 131 to the blood treatment device 11, a first valve V1 is arranged in or within the dialysate circuit 13.

In the drain line 137 leading from the blood treatment device 11 to the dialysate outlet 133, a second valve V2 is arranged.

The supply line 135 and the drain line 137 of the dialysate circuit 13 are in fluid communication via a connection line 139 which optionally comprises a bypass valve V3.

As shown in FIG. 1, a radiation receptor 15 is arranged within the arterial blood line 1 of the extracorporeal blood circuit.

The radiation receptor 15 may be an optical detector. The radiation receptor 15 may, e.g., be provided and/or designed and/or configured and/or intended for detecting changes in the light intensity of emitted and received radiation, caused by the presence and possibly the motion of the red blood cells of the blood flowing extracorporeally.

The radiation receptor 15 may, as shown here in FIG. 1, be designed integrally, i.e., in one shared or common body with a radiation source 17, e.g., a infrared source.

In other embodiments, not shown here, radiation receptor 15 and radiation source 17 may, however, also be designed physically separated from each other and/or arranged spatially separated from each other.

For detecting a potential leakage in the section 100 of the system 1000, in an exemplary embodiment of the method according to the present invention initially the shut-off device 7 and the valves V1 and V2 in the dialysate circuit 13 are closed.

In certain embodiments of the method according to the present invention, this may be carried out without changing a yet present, constant rotational speed of the conveying device 5 or without setting another constant rotational speed than one of those constant rotational speeds which are used during a patient's treatment anyway or regularly. In other embodiments, the rotational speed of the conveying device 5, however, may definitely change or be changed in order to perform the method as described herein.

Valve V3—if present—is opened subsequently.

This way, a static pressure difference is built up across the conveying device 5.

During the first conveying state reached or set herewith which in absence of a leak/a leakage downstream the conveying device 5 is or may be 0 ml/min (in words: zero), the radiation receptor 15 receives that proportion of the emitted radiation which is reflected by the blood. This proportion is to be understood as the first proportion.

In order to record a further proportion, denoted as second proportion, of the light emitted by the radiation source 17 in a second conveying state of the conveying device 5 for reference, the conveying device 5 is stopped for a certain amount of time. The second conveying state therefore reliably corresponds to a flow standstill of the blood within the considered section of the extracorporeal blood circuit.

The signal recorded during a flow standstill (second proportion) of the second conveying state is compared to the signal related to or obtained from the rotating conveying device 5 (first proportion) of the first conveying state.

After an undetermined or predetermined, in any case sufficient, amount of time, the conveying device 5 is restarted.

In case the first proportion differs from the second proportion, e.g., when considering their average values, of the unchangedly emitted optical signal, i.e., between the continuously rotating conveying device 5 and the stillstanding conveying device 5, the presence of a blood leak within the extracorporeal blood circuit, e.g., a leakage in one of the two patient lines 1, 3 of a tubing set and/or a leakage in a connection to the blood treatment device 11 may be inferred or assumed. A corresponding alarm signal may be issued.

If no change in the signal or in its average value or another mathematical evaluation thereof is detected, the leakage test is passed.

Also possible and contemplated according to the present invention is the following approach: With valve V2 being closed, a liquid, e.g., dialysate, is conveyed across the membrane of the blood treatment device 11 to the blood side by means of the dialysate pump (not shown) or another accordingly switched pump. There, the liquid transported to the blood side disperses to both the venous line section 4 and the arterial line section 6. Across or over each the drip chamber 2 and the, in particular during standstill, overflowable conveying device 5, also the arterial blood line 1 and the venous blood line 3 may be rinsed. This way, the whole system 1000 may be filled with liquid. The arterial blood line 1 and the venous blood line 3 may thereby directly or via an adapter, or the like, be short-circuited or connected to each other. Alternatively, the arterial blood line 1 and the venous blood line 3 are not connected with each other. The liquid flowing through the lines may be discarded. Subsequent to the approach described herein, the conveying device 5 may be operated in order to remove air possibly present in the system 1000 from the system 1000 by means of the drip chamber 2 or its ventilation device.

In the following FIGS. 2 to 4, in each case the course of the optical signal of the reflected radiation is represented as a number proportional to the light intensity over the time t, respectively. In FIG. 5, instead, the course of the optical signal of the transmitted radiation is represented measured as a number proportional to the light intensity over the time t (e.g., in seconds or another unit).

For easier understanding, in the following experiment descriptions of FIGS. 2 to 5, the reference numerals of the components shown in the section 100 of the system 1000 according to the present invention are used each, even though these components are partly not shown in the figures described in the following.

Figure 2:
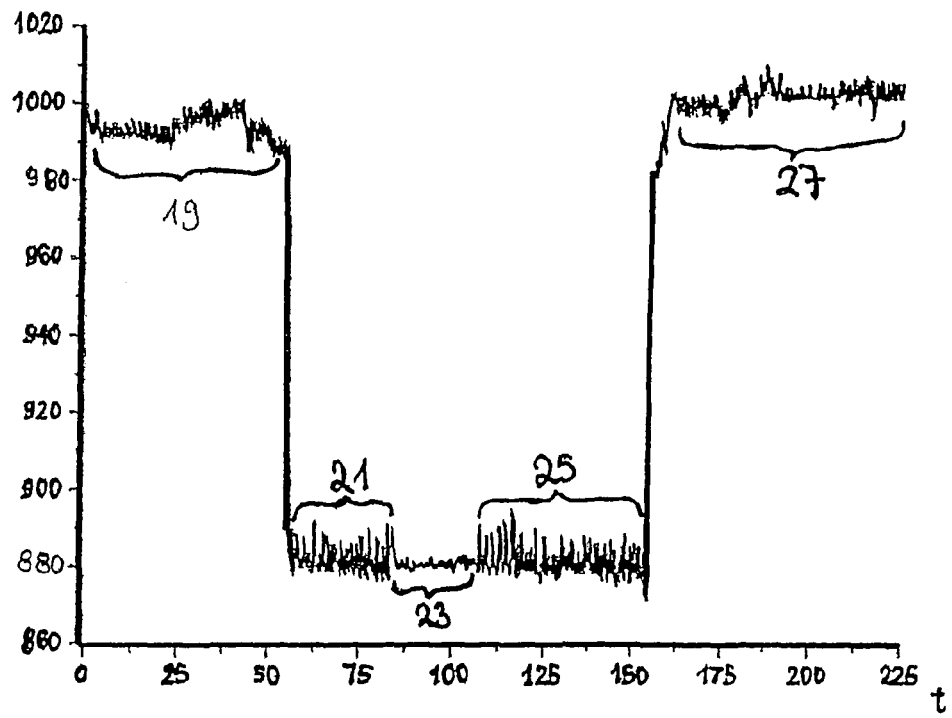
FIG. 2 shows the course of an optical signal in a test set-up without leakage.

FIG. 2 shows the course of the optical signal in a test set-up without leakage.

In this test set-up, which has led to the result of FIG. 2, the conveying device 5 was initially operated with a continuous rotational speed of 4500 rpm. The tubing set did not have a leakage.

The shut-off device 7 was initially open (area 19). Without changing the rotational speed of the conveying device 5, the shut-off device 7 was closed after a little bit more than 50 time units (area 21; corresponds to the first conveying state). In FIG. 2, the average value of the first proportion of the received radiation is easily recognizable at about 880 units of measurement or dimensional units.

Subsequently, the conveying device 5 was stopped (area 23; corresponds to the second conveying state) and a little bit later on, e.g., after 25 time units as shown in FIG. 2, restarted (area 25). The average value of the second proportion of the received radiation is also at about 880 units of measurement or dimensional units.

A difference between the two average values (first proportion and second proportion) thus results in about ±0 measurement or dimensional units.

A comparison of the difference and a threshold value (not indicated here) would thus—due to lack of a difference—lead to the result that a leakage is not detectable.

Towards the end of the experiment, the shut-off device 7 is re-opened (area 27).

The experiment as described by means of the course of the curve of FIG. 2 was repeated with specifically placed leakages within the tubing set: In the implementations of the tests shown in FIGS. 3 to 5, an open syringe (without piston) was pricked into a septum, respectively. This way, by choice of the cannula, a leak of pre-defined size could be created.

Figure 3:
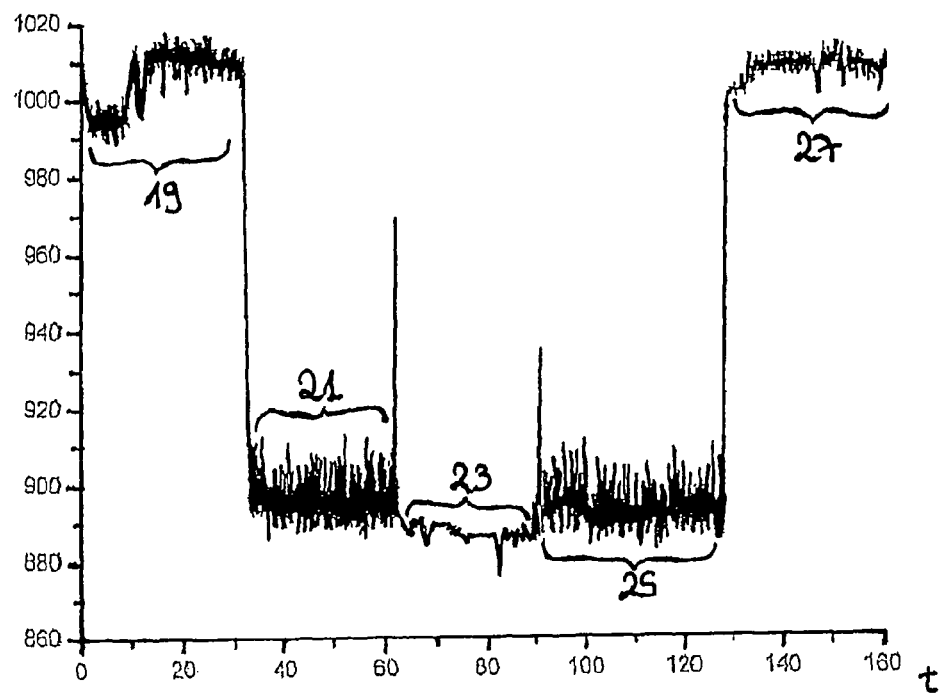
FIG. 3 shows the course of an optical signal in case of a leakage generated by means of a 0.4×19 mm-cannula.

FIG. 3 shows the course of an optical signal with a leakage due to puncture of the tubing set by means of a 0.4×19 mm-cannula.

As can be taken from FIG. 3, the average value of the optical signal related to or obtained from the conveying device 5 being circulating or conveying and the shut-off device 7 being closed (area 21; average value is at about 889 dimensional units) is, unlike during the experiment without leakage (FIG. 2), higher than related to or obtained from the conveying device 5 standing still (area 23; average value is at about 881 dimensional units). The difference value was about 8 dimensional units. This may be the result of the very low blood flow possible due to the leakage.

The measurement or dimensional units may be, e.g., counts which are obtained as follows: The signal receiving device as used in the examples of the figures as described herein is a light receptor which is designed or embodied as a light-to-frequency-converter. The sensor used thus outputs a frequency proportional to the light intensity received. For the evaluation, e.g., the edges of the signal are counted for a certain time unit; each edge is thereby classified as a count.

With a correspondingly determined threshold value, by comparing a difference hereto, a leakage alarm may be issued.

Figure 4:
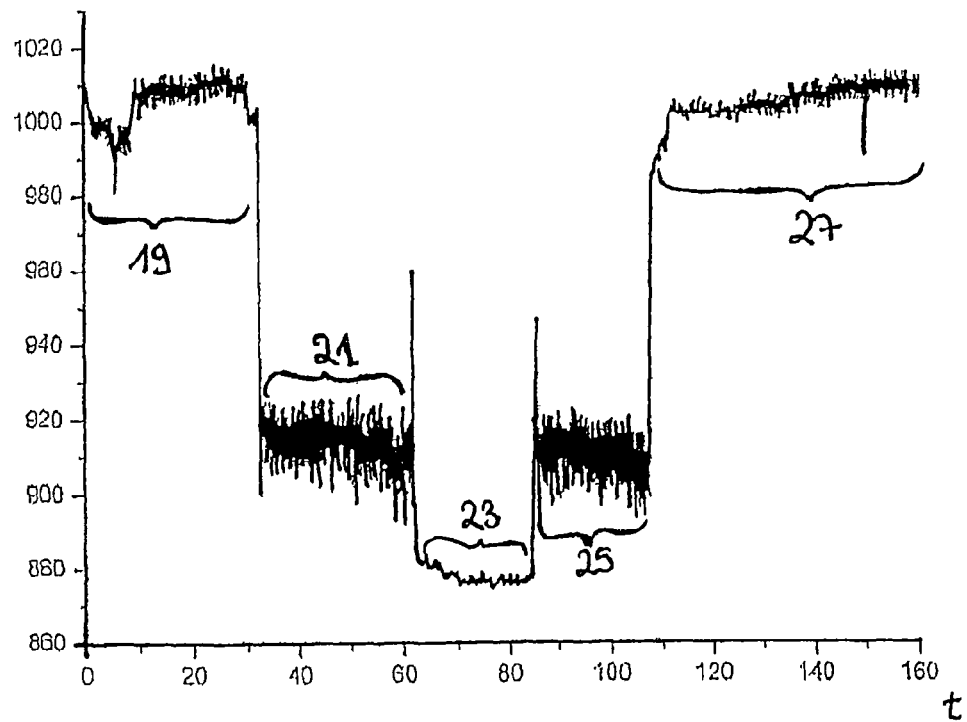
FIG. 4 shows the course of an optical signal in case of a further leakage generated by means of a 0.6×25 mm-cannula.
Figure 5:
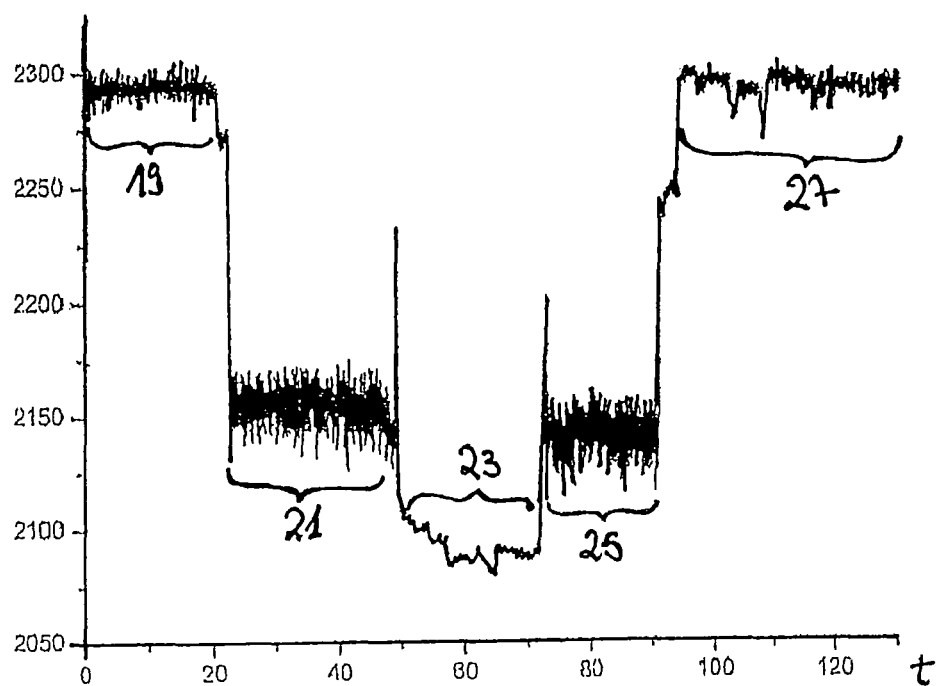
FIG. 5 shows the course of an optical signal in case of a still further leakage generated by means of a 0.6×25 mm-cannula, during a transmittance measurement.

FIG. 4 shows the course of an optical signal with a leakage created by means of a 0.6×25 mm-cannula during a reflection measurement.

In FIG. 4, it is easily recognizable that the signal course related to our obtained from a circulating conveying device 5 and a closed shut-off device 7 is significantly higher than the signal course related to or obtained from a stillstanding conveying device 5.

The higher signal difference of FIG. 4—as compared to the course of FIG. 3—may be attributed to the larger leakage created by means of the 0.6×25 mm-cannula in FIG. 4 as compared to the one created by means of the 0.4×19 mm-cannula from FIG. 3 and the thus admitted larger flow (despite the shut-off).

FIG. 5 shows the course of an optical signal with a leakage created by a 0.6×25 mm-cannula during a transmittance measurement. Apart from that, anything that was said regarding FIGS. 2 to 4 applies.

Reference numeral list

| reference numeral | description |
|---|---|
| 1000 | system |
| 100 | section |
| 1 | arterial blood line |
| 2 | drip chamber |
| 3 | venous blood line |
| 31 | venous chamber |
| 4 | venous line section |
| 5 | conveying device |
| 6 | arterial line section |
| 7 | shut-off device (venous clamp) |
| 9 | arterial clamp |
| 11 | blood treatment device |
| 13 | dialysate circuit |
| 131 | dialysate inlet |
| 133 | dialysate outlet |
| 135 | supply line |
| 137 | drain line |
| 139 | connection line |
| 15 | radiation receptor |
| 17 | radiation source |
| 19 | areas in the course of the radiation signal |
| 21 | |
| 23 | |

-continued

Reference numeral list

| reference numeral | description |
|---|---|
| 25 | |
| 27 | |
| V1, V2 | valves within the dialysate circuit |
| V3 | bypass valve within the dialysate circuit (optional) |

What is claimed is:

1. A method for detecting leakages in a system, the system including:
a section;
at least one conveying device for conveying medical fluid through the section; and
a shut-off device arranged downstream from the section and configured to interrupt or reduce the medical fluid flowing through the section or out of the section into an area downstream of the shut-off device,
wherein the method comprises:
interrupting or reducing the medical fluid flowing through the section or out of the section by setting or adjusting the shut-off device to obtain a first conveying state;
adjusting at least one parameter of the at least one conveying device to stop or throttle the at least one conveying device in a second conveying state;
emitting at least one signal via a signal emitting device into the section in the first and the second conveying state;
receiving a first portion of the emitted signal leaving the section via a signal receiving device in the first conveying state;
receiving a second portion of the emitted signal leaving the section via the signal receiving device in the second conveying state; and
determining whether a leakage is present by comparing the first portion to the second portion.

2. The method according to claim 1, wherein the emitted signal comprises ultrasonic waves, wherein the signal emitting device emits ultrasonic waves, and wherein the signal receiving device detects ultrasonic waves.

3. The method according to claim 1, wherein the emitted signal comprises radiation, wherein the signal emitting device is a radiation source for emitting radiation, and wherein the signal receiving device is a radiation receptor for receiving or detecting radiation.

4. The method according to claim 3, wherein the emitted radiation comprises electromagnetic radiation.

5. The method according to claim 4, wherein the emitted radiation comprises infrared radiation.

6. The method according to claim 1, wherein the first and/or second portion leaving the system is reflected, transmitted or scattered radiation.

7. The method according to claim 1, wherein determining whether a leakage is present by comparing the first portion to the second portion comprises:
calculating the difference of the first and the second portion and comparing the difference to a threshold value; and/or
comparing the first portion and the second portion to the threshold value.

8. The method according to claim 1, wherein the first and/or the second portion is a percentage of an intensity of the emitted signal or of the emitted radiation.

9. The method according to claim 1, wherein the signal reception device is further used or applicable or usable or provided or intended for detecting an optical density or a change thereof.

10. The method according to claim 1, wherein the flowing of the medical fluid is stopped via the shut-off device in the first conveying state.

11. The method according to claim 1, wherein the conveying device is stopped in the second conveying state.

12. The method according to claim 1, wherein a centrifugal pump is used as the conveying device.

13. The method according to claim 1, wherein an alarm is issued when a leakage is detected.

14. A system including a treatment cassette, the system comprising:
 at least one section;
 a conveying device for conveying medical fluid through the section;
 a shut-off device for interrupting or reducing the medical fluid flowing through the section;
 a signal emitting device for emitting a signal;
 a signal receiving device for receiving a portion of the emitted signal; and
 a controller configured to execute the method according to claim 1.

15. The system according to claim 14, wherein the signal emitting device is a radiation source for emitting radiation, and wherein the signal receiving device is a signal receptor for receiving a portion of the emitted radiation.

16. The system according to claim 14, further comprising:
 a comparing device for comparing the first portion of the emitted signal received in the first conveying state and the second portion of the emitted signal received in the second conveying state.

17. The system according to claim 14, further comprising:
 a determination device for determining whether a leakage is present by comparing the first portion to the second portion.

18. The system according to claim 14, wherein at least the conveying device is part of the treatment cassette.

19. The system according to claim 14, wherein the signal emitting device is configured as a radiation source for emitting electromagnetic radiation.

20. The system according to claim 14, wherein the signal receiving device is configured to detect reflected and/or transmitted and/or scattered radiation.

21. The system according to claim 14, further comprising:
 an alarming device configured to issue an alarm when a leakage is detected.

22. A medical-technical treatment device, configured to execute the method according to claim 1.

23. A non-transitory computer-readable storage medium with an executable program stored thereon, wherein the program is configured to instruct a programmable computer system to execute the steps of the method according to claim 1.

* * * * *